(12) United States Patent
Zhuan (10) Patent No.: US 7,266,855 B2
(45) Date of Patent: Sep. 11, 2007

(54) ELECTRIC TOOTHBRUSH

(76) Inventor: Qingping Zhuan, 5980 Whitehorn Avenue Unit 110, Mississauga (CA) L5V 2Y5

( * ) Notice: Subject to any disclaimer, the term of this patent is extended or adjusted under 35 U.S.C. 154(b) by 693 days.

(21) Appl. No.: 10/160,034

(22) Filed: Jun. 4, 2002

(65) Prior Publication Data

US 2003/0221269 A1 Dec. 4, 2003

(51) Int. Cl.
  *A46B 13/02* (2006.01)
(52) U.S. Cl. .......................... 15/22.4; 15/22.1
(58) Field of Classification Search ............. 15/22.1, 15/22.2, 28, 22.4, 21.1
  See application file for complete search history.

(56) References Cited

U.S. PATENT DOCUMENTS

| | | | |
|---|---|---|---|
| 4,371,341 A * | 2/1983 | Nakanishi ............... 433/118 |
| 4,432,729 A * | 2/1984 | Fattaleh ................... 433/118 |
| 4,461,053 A | 7/1984 | Nitzsche et al. |
| 4,479,516 A | 10/1984 | Hunter |
| 4,543,679 A | 10/1985 | Rosofsky et al. |
| 5,353,460 A | 10/1994 | Bauman |
| 5,359,747 A | 11/1994 | Amakasu |
| 5,404,608 A | 4/1995 | Hommann |
| 5,416,942 A | 5/1995 | Baldacci et al. |
| 5,435,034 A | 7/1995 | Bigler et al. |
| 5,442,827 A | 8/1995 | Hommann |
| 5,448,792 A | 9/1995 | Wiedemann et al. |
| 5,461,744 A | 10/1995 | Merbach |
| 5,467,494 A | 11/1995 | Muller et al. |
| 5,487,877 A | 1/1996 | Choi |
| 5,493,747 A | 2/1996 | Inakagata et al. |
| 5,499,420 A | 3/1996 | Boland |
| D368,373 S | 4/1996 | Shimatsu et al. |
| 5,504,958 A | 4/1996 | Herzog |
| 5,504,959 A | 4/1996 | Yukawa et al. |
| 5,504,960 A | 4/1996 | Hommann |
| 5,504,961 A | 4/1996 | Yang |
| D370,125 S | 5/1996 | Craft et al. |
| 5,524,312 A | 6/1996 | Tan et al. |
| D371,242 S | 7/1996 | Shimatsu et al. |
| 5,561,881 A | 10/1996 | Klinger et al. |
| D375,204 S | 11/1996 | Okada |
| 5,575,380 A | 11/1996 | Imai |
| 5,577,285 A | 11/1996 | Drossler |
| 5,579,786 A | 12/1996 | Wolk et al. |
| 5,590,434 A | 1/1997 | Imai |
| 5,613,258 A | 3/1997 | Hilfinger et al. |
| 5,617,603 A | 4/1997 | Mei |

(Continued)

*Primary Examiner*—Gladys J P Corcoran
*Assistant Examiner*—Laura C Guidotti
(74) *Attorney, Agent, or Firm*—Bereskin & Parr (57) ABSTRACT

The present invention is directed towards an electric toothbrush having a replaceable tuft assembly. The electric toothbrush comprises a main body, an electric motor mounted in the main body, a support member coupled to the main body, a tuft assembly which is releasably attachable to the support member and a transmission that is operatively connected to the electric motor to provide rotational motion to the tuft assembly. The support member has a first connection member and the tuft assembly has a second connection member. The first and second connection members are adapted to allow rotational motion of the tuft assembly with respect to the main body. In another aspect, the toothbrush may further comprise an adaptor that is releasably attachable to the tuft assembly and converts the rotational motion from the transmission to reciprocal rotational motion for urging the tuft assembly to reciprocally rotate.

11 Claims, 10 Drawing Sheets

U.S. PATENT DOCUMENTS

| | | | |
|---|---|---|---|
| 5,625,916 A * | 5/1997 | McDougall | 15/28 |
| 5,651,157 A | 7/1997 | Hahn | |
| D382,407 S | 8/1997 | Craft et al. | |
| 5,652,990 A | 8/1997 | Driesen et al. | |
| D385,702 S | 11/1997 | Okada | |
| 5,697,117 A | 12/1997 | Craft | |
| RE35,712 E | 1/1998 | Murayama | |
| D388,958 S | 1/1998 | Hartwein | |
| 5,727,273 A | 3/1998 | Pai | |
| 5,732,432 A | 3/1998 | Hui | |
| 5,732,433 A | 3/1998 | Gocking et al. | |
| D394,751 S | 6/1998 | Eguchi et al. | |
| 5,784,742 A | 7/1998 | Giuliani et al. | |
| 5,784,743 A | 7/1998 | Shek | |
| D396,957 S | 8/1998 | Allende | |
| D397,251 S | 8/1998 | Eguchi et al. | |
| D397,252 S | 8/1998 | Allende | |
| 5,791,007 A | 8/1998 | Tsai | |
| 5,794,296 A | 8/1998 | Wong | |
| 5,796,325 A | 8/1998 | Lundell et al. | |
| 5,822,821 A | 10/1998 | Sham | |
| RE35,941 E | 11/1998 | Stansbury, Jr. | |
| 5,836,030 A | 11/1998 | Hazeu et al. | |
| 5,842,244 A | 12/1998 | Hilfinger et al. | |
| 5,842,245 A | 12/1998 | Pai | |
| 5,850,655 A | 12/1998 | Gocking et al. | |
| 5,862,558 A | 1/1999 | Hilfinger et al. | |
| 5,862,559 A | 1/1999 | Hunter | |
| 5,867,856 A | 2/1999 | Herzog | |
| 5,930,858 A | 8/1999 | Jung | |
| 5,934,908 A | 8/1999 | Woog et al. | |
| 5,943,723 A | 8/1999 | Hilfinger et al. | |
| 5,974,613 A | 11/1999 | Herzog | |
| 5,974,615 A | 11/1999 | Schwarz-Hartmann et al. | |
| 5,987,681 A | 11/1999 | Hahn et al. | |
| 6,000,083 A | 12/1999 | Blaustein et al. | |
| 6,021,538 A | 2/2000 | Kressner et al. | |
| 6,092,252 A | 7/2000 | Fischer et al. | |
| 6,138,310 A | 10/2000 | Porper et al. | |
| 6,178,579 B1 | 1/2001 | Blaustein et al. | |
| 6,189,693 B1 | 2/2001 | Blaustein et al. | |
| D440,766 S | 4/2001 | Hartwein et al. | |
| 6,230,354 B1 | 5/2001 | Sproat | |
| 6,230,717 B1 | 5/2001 | Marx et al. | |
| 2001/0004781 A1 | 6/2001 | Blaustein et al. | |
| 2001/0014990 A1 | 8/2001 | Fritsch et al. | |
| 2001/0020314 A1 | 9/2001 | Calabrese | |
| 2001/0023516 A1 | 9/2001 | Driesen et al. | |
| 2003/0097723 A1* | 5/2003 | Li | 15/22.1 |

* cited by examiner

ELECTRIC TOOTHBRUSH

FIELD OF THE INVENTION

This invention relates to an electric toothbrush having a rotatable tuft assembly. In another aspect, this invention relates to an electric toothbrush having a replaceable rotatable tuft assembly.

BACKGROUND OF THE INVENTION

Electric toothbrushes are popular since these toothbrushes can provide a higher level of cleaning compared to that obtainable with manual toothbrushes. In general, electric toothbrushes comprise a base which functions as a handle, a shaft that extends from the base, and a tuft assembly (i.e. brush head), having bristles, located at the distal end of the shaft. The electric toothbrush further comprises an electric motor located in the base and a transmission located in the base and/or the shaft. During use, the electric motor provides rotational energy to the transmission which in turn provides rotational motion to the tuft assembly to provide brushing action to clean the teeth of the electric toothbrush user.

The bristles on the tuft assembly can become worn due to usage over time and should be replaced. In this case, some electric toothbrushes provide a shaft that is removably attachable to the base of the electric toothbrush so that the tuft assembly can be replaced. However, the cost of replacing the tuft assembly is increased since both the shaft and the tuft assembly are replaced while usually only the tuft assembly needs to be replaced.

SUMMARY OF THE INVENTION

The present invention is directed towards an electric toothbrush that has a main body with an electric motor mounted therein. The toothbrush has a tuft assembly that is rotatably coupled to the main body, and a transmission that is operatively connected to the electric motor to provide rotational motion to the tuft assembly. The toothbrush also has an adaptor that is pivotally connected to the tuft assembly and also slidably connected to the transmission. The adaptor converts the rotational motion from the transmission to provide reciprocal rotational motion to the tuft assembly.

In another aspect, the invention is directed towards an electric toothbrush having a replaceable tuft assembly. The electric toothbrush comprises a main body, an electric motor mounted in the main body, a support member coupled to the main body, a tuft assembly which is releasably attachable to the support member and a transmission that is operatively connected to the electric motor to provide rotational motion to the tuft assembly. The support member has a first connection member and the tuft assembly has a second connection member. The first and second connection members are adapted to allow rotational motion of the tuft assembly with respect to the main body.

In another aspect, the present invention is directed to an electric toothbrush comprising a main body, an electric motor mounted in the main body, a support member coupled to the main body, a tuft assembly releasably attachable to the support member, a transmission operatively connected to the electric motor and adapted to provide rotational motion to the tuft assembly, and an adaptor. The adaptor can be releasably connectable to the tuft assembly and converts the rotational motion from the transmission to reciprocal rotational motion for urging the tuft assembly to reciprocally rotate. Furthermore, the support member has a first connection member and the tuft assembly has a second connection member. The first and second connection members are adapted to allow rotational motion of the tuft assembly with respect to the main body.

BRIEF DESCRIPTION OF THE DRAWINGS

For a better understanding of the present invention and to show more clearly how it may be carried into effect, reference will now be made, by way of example only, to the accompanying drawings which show preferred embodiments of the present invention and in which:

FIG. 3b is an exploded perspective bottom view of the tuft assembly and the adaptor of FIG. 3a;

FIG. 3c is an exploded perspective view of the portion of the electric toothbrush shown in FIG. 3a;

FIG. 4a is an exploded cross-sectional side view of a portion of the electric toothbrush of FIG. 1 showing an alternative embodiment of the tuft assembly and the adaptor of FIG. 3a;

FIG. 4b is an exploded perspective bottom view of the tuft assembly and the adaptor of FIG. 4a;

FIG. 4c is an exploded perspective view of the portion of the electric toothbrush shown in FIG. 4a;

FIG. 5b is an exploded cross-sectional view of FIG. 5a;

FIG. 5c is an exploded cross-sectional, perspective view of the electric toothbrush of FIG. 5a;

FIG. 5d is an exploded perspective view of the electric toothbrush of FIG. 5a;

FIG. 8b is an exploded front perspective view of a portion of the electric toothbrush of FIG. 8a;

FIG. 8c is an exploded rear perspective view of a portion of the electric toothbrush of FIG. 8a;

FIG. 9b is an exploded front perspective view of a portion of the electric toothbrush of FIG. 9a; and, FIG. 9c is an exploded rear perspective view of a portion of the electric toothbrush of FIG. 9a.

DETAILED DESCRIPTION OF THE INVENTION

Figure 1:
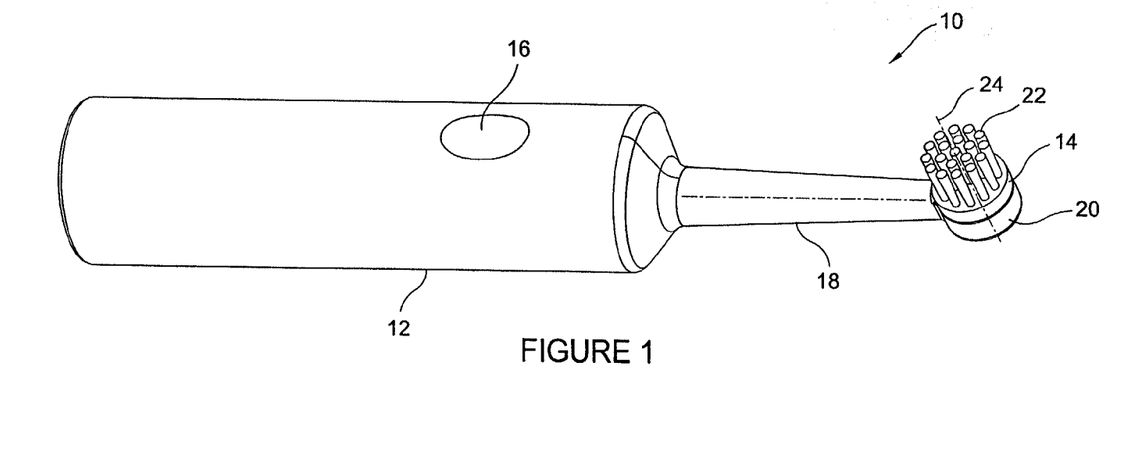
FIG. 1 is a perspective view of an electric toothbrush.

Referring now to FIG. 1, shown therein is an electric toothbrush 10 having a main body 12, a tuft assembly 14 and an actuation means 16. The main body 12 further comprises a shaft 18 and a support member 20. The tuft assembly 14 is removably connectable to the support member 20 as will be described further below. The tuft assembly 14 has a plurality of bristles 22 which are used to clean the teeth of the user of the electric toothbrush 10. As shown, the bristles 22 may be in a circular arrangement and extend along an axis that is generally orthogonal to the shaft 18. Alternatively, the bristles 22 may have another suitable arrangement and extend along an axis that is at some other angle with respect to the shaft 18.

In use, the user of the electric toothbrush 10 activates the electric toothbrush 10 via the actuation means 16, which may be a button, a toggle switch, a slide switch or the like. When the electric toothbrush 10 is active, the tuft assembly 14 rotates in a reciprocating fashion about brush rotation axis 24 to provide a back-and-forth brushing action. The user of the electric toothbrush 10 then applies the bristles 22 to his or her teeth to clean the teeth as required.

Figure 2:
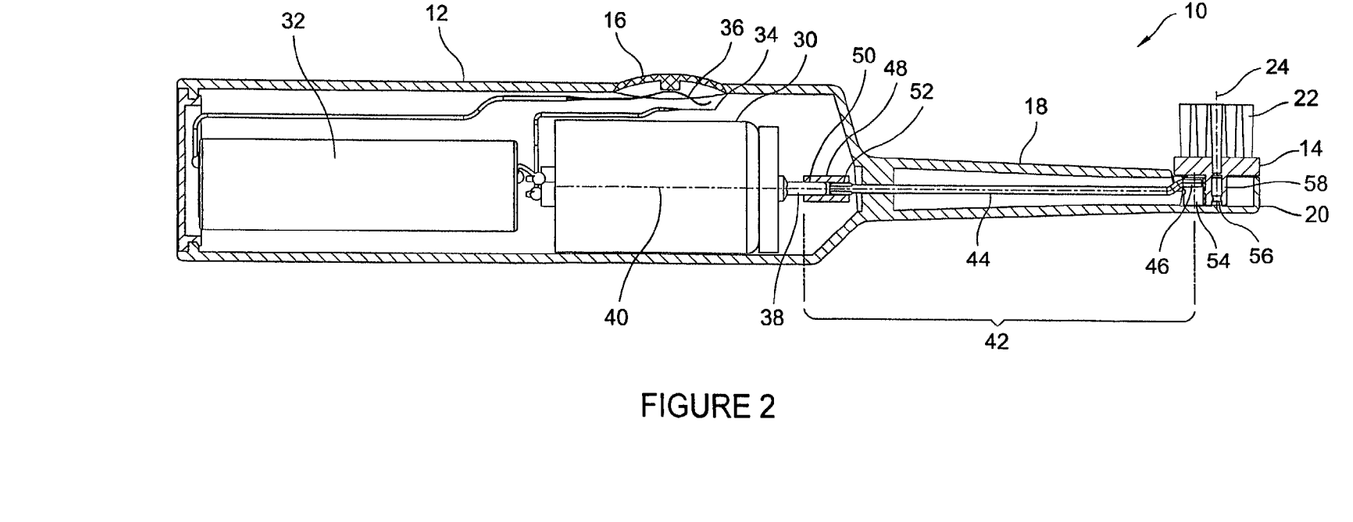
FIG. 2 is a cross-sectional side view the electric toothbrush of FIG. 1.

Referring now to FIG. 2, the electric toothbrush 10 further comprises an electric motor 30, a power source 32 and electrical leads 34 and 36 which together form an electrical circuit. When the actuation means 16 is actuated to activate the electric toothbrush 10, the electrical leads 34 and 36 come into contact to supply power to the electric motor 30 from the power source 32. The electric motor 30, which is mounted in the main body 12, may be any suitable compact electric motor. The power source 32 may preferably be a battery, but may alternately be a connection to an external power source, such as, for example, an electric wire and plug for connection to a standard 120 Volt AC source.

The electric motor 30 has an output shaft 38 that rotates about motor axis 40 when the electric toothbrush 10 is active. The output shaft 38 is drivingly connected to a transmission 42 to provide rotational motion to the tuft assembly 14. In this embodiment, the transmission 42 comprises a drive shaft 44 having an eccentric end 46 and a connector 48 having first and second ends 50 and 52. The connector 48 has a slot in the first end 50 to couple with the output shaft 38 of the electric motor 30. The connector 48 also has a slot in the second end 52 to couple with the drive shaft 44. These slots may have any shape necessary to provide coupling with the aforementioned parts.

The main body 12 surrounds the electric motor 30, the power source 32 and the transmission 42 and can provide a base for mounting these parts. The main body 12 is made from a suitable, water impermeable plastic to prevent water from damaging the internal components of the electric toothbrush 10 and to prevent a user from potential harm during use. Alternatively, the main body 12 may be made from other suitable, water impermeable materials, such as a suitable metal, or from a composite of materials such as metal and plastic.

Figure 3A:
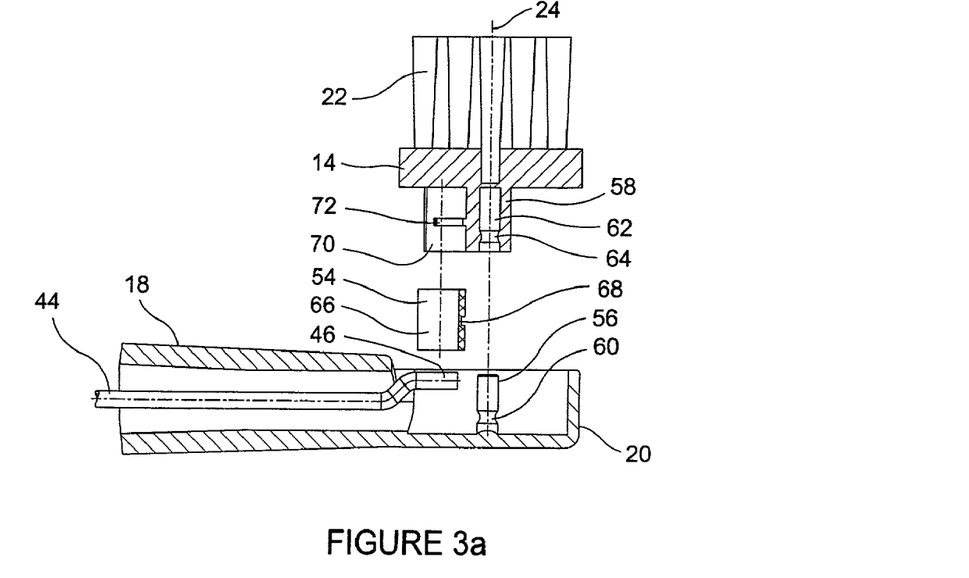
FIG. 3a is an exploded cross-sectional side view of a portion of the electric toothbrush of FIG. 1 showing a tuft assembly and an adaptor.
Figures 3B, 3C:
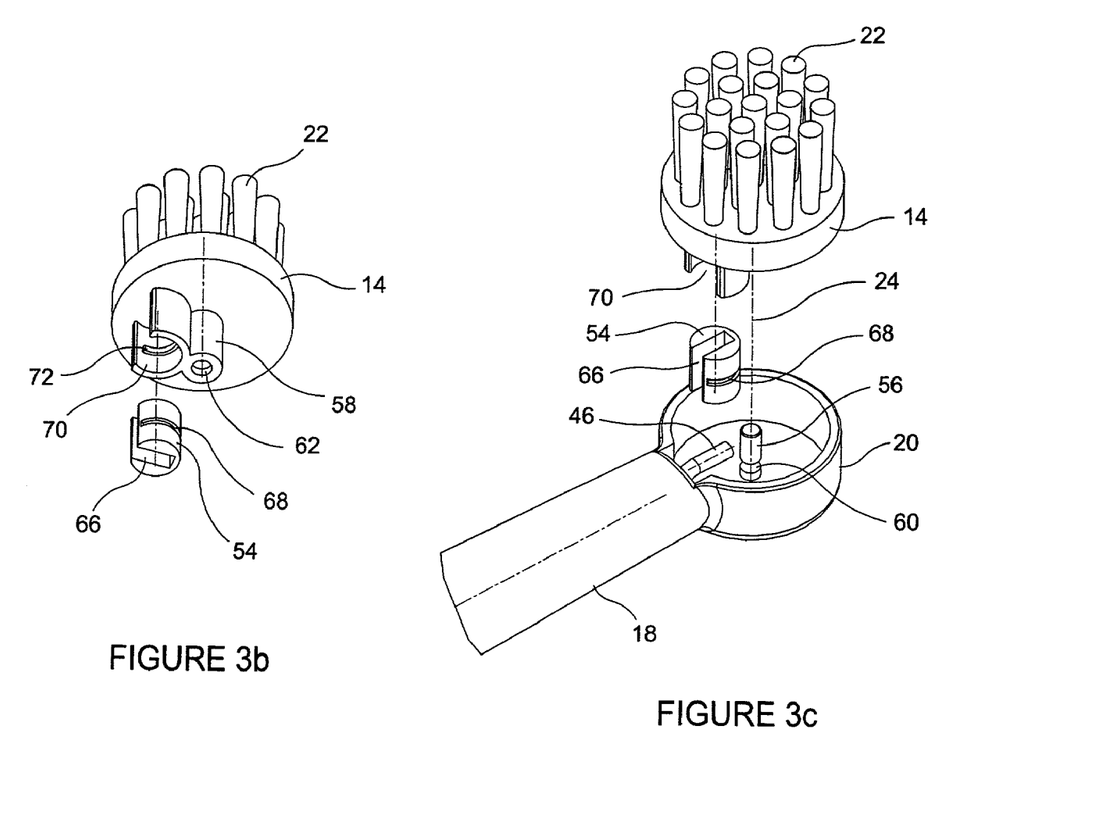

Referring now to FIGS. 3a to 3c, the support member 20 has a first connection member 56 and the tuft assembly 14 has a second connection member 58. The first connection member 56 comprises an elongate body with a groove 60 on an outer surface thereof. The second connection member comprises a cylindrical body having an inner channel 62 with a rib 64. The first and second connection members 56 and 58 are dimensioned to be releasably attachable by "snapping" the first and second connection members 56 and 58 apart from each other so that the tuft assembly 14 may be replaced when it is damaged or the bristles 22 are worn down to the point that they can no longer provide sufficient cleaning action. The first and second connection members 56 and 58 are also dimensioned so that the second connection member 58 may rotate about the first connection member 56. Accordingly, the inner channel 62, not including the portion having the rib 64, has a diameter which is generally slightly larger than the diameter of the elongate body of the first connection member 56, not including the portion having the groove 60, so that the inner channel 62 may receive the elongate body while also allowing for rotational movement of the second connection member 58 about the central vertical axis of the first connection member 56. To ensure that the second connection member 58 remains mounted about the first connection member 56 when the electric toothbrush 10 is active, the inner channel 62 has a rib 64 that engages the groove 60 of the elongate body. The rib 64 and the groove 60 facilitate the snap-action alluded to earlier. Once again, to ensure rotation of the second connection member 58 about the axis of the first connection member 56, there is some space between the rib 64 and the groove 60. In addition, to ensure that the tuft assembly 14 is removably attachable to the support member 20, at least one of the first and second connection members 56 and 58 is made from a resilient material. In an alternative embodiment, the position of the first and second connection members 56 and 58 may be reversed, i.e., the first connection member 56 may be located on the tuft assembly 14 and the second connection member 58 may be located on the support member 20.

Still referring to FIGS. 3*a* to 3*c*, the tuft assembly 14 further comprises an adaptor 54 that is used to transform the rotational motion of the drive shaft 44 into reciprocating rotational motion to facilitate the forward-and-backward brushing action of the electric toothbrush 10. In this embodiment, the adaptor 54 comprises a cylindrical body having a slot 66 and a first coupling member 68. The slot 66 is dimensioned to accommodate the eccentric end 46 of the drive shaft 44 and has a vertical extent that accommodates the vertical displacement of the tip of the eccentric end 46 as the drive shaft 44 rotates while the electric toothbrush 10 is in operation. The first coupling member 68 may be at least one groove shaped so that the adaptor 54 releasably engages the tuft assembly 14 (although only one groove is shown in FIGS. 3*a* to 3*c*).

The tuft assembly 14 further comprises an inner recess 70 and a second coupling member 72. The inner recess 70 is shaped to receive the adaptor 54. Accordingly, since the adaptor 54 has a cylindrical body in this embodiment, the inner recess 70 has a cylindrical, concave shape to mate with the adaptor 54 when the adaptor 54 is placed within the inner recess 70. In addition, the second coupling member 72 may be at least one rib (although only one rib is shown in FIGS. 3*a* to 3*c*) which is shaped to releasably engage the at least one groove on the adaptor 54 when the adaptor 54 is placed within the inner recess 70 of the tuft assembly 14. In addition, the adaptor 54, the inner recess 70 and the first and second coupling members 68 and 72 are shaped so that the adaptor 54 may preferably freely move with respect to the inner recess 70 or the tuft assembly 14. However, the adaptor 54 is always retained within the recess 70 when the toothbrush 10 is in operation. Accordingly, the at least one groove (i.e. the first coupling member 68) may not totally encircle the adaptor 54 but may extend along only a portion of the circumference of the adaptor 54 while still engaging the at least one rib (i.e. the second coupling member 72) which may correspondingly extend along only a portion of the circumference of the inner recess 70. However, the dimension of the first and second coupling members 68 and 72 must cooperate with the motion of the eccentric end 46 of the transmission 42 as discussed below.

Figure 4A:
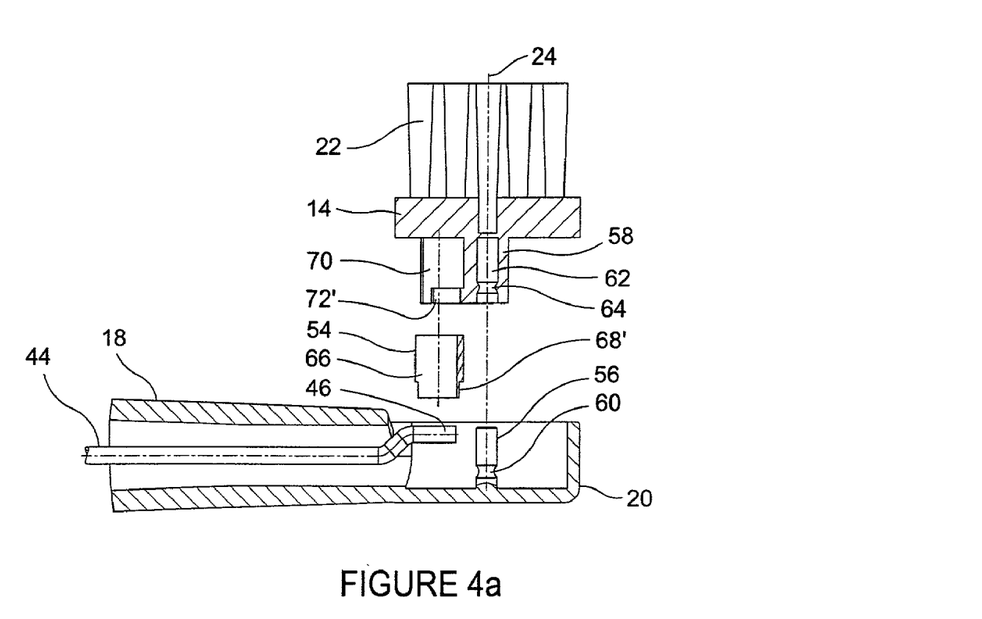
Figure 4B:
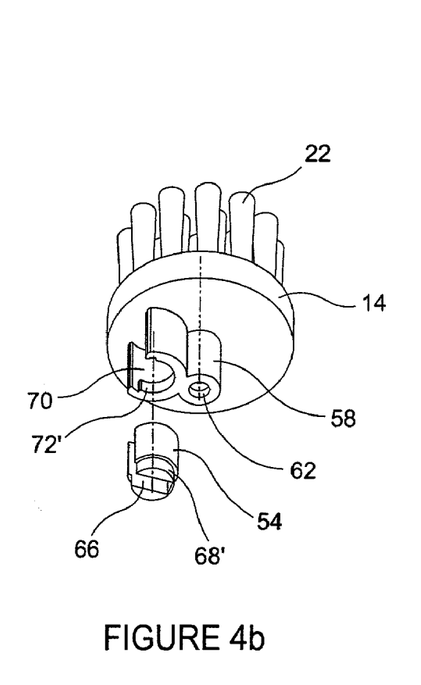
Figure 4C:
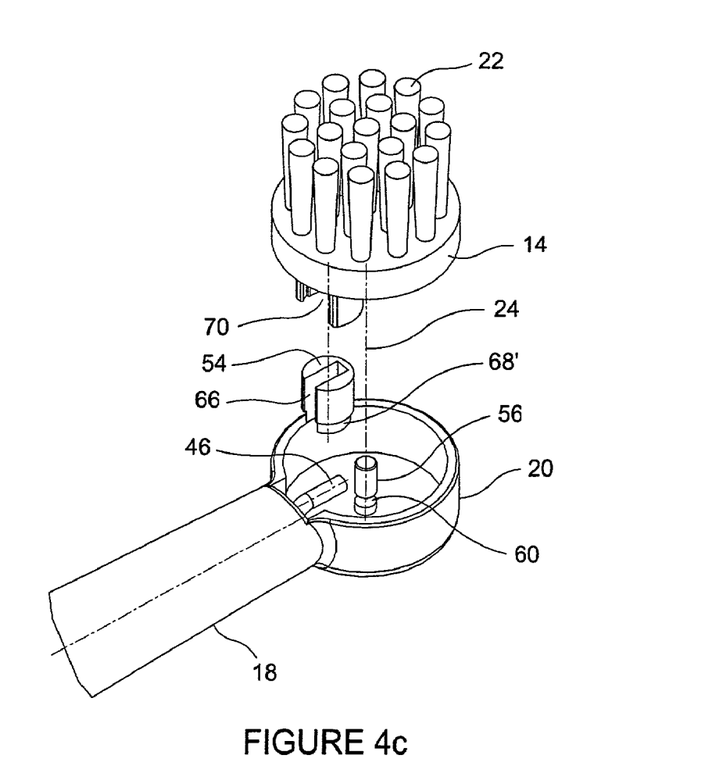

In alternative embodiments, the shape of the adaptor 54 and the inner recess 70 may be varied. For instance, referring to FIGS. 4*a* to 4*c*, the first coupling member 68' may be a groove located at the bottom of the adaptor 54 and the second coupling member 72' may be a rib located at the bottom of the inner recess 70 (i.e. see FIGS. 4*a* to 4*c*). In a further alternative embodiment, the first coupling member 68 may be at least one rib and the second coupling member 72 may be at least one groove located in a complementary fashion to the first coupling member 68.

In the embodiments of FIGS. 3*a* to 3*c* and 4*a* to 4*c*, either the tuft assembly 14 or the adaptor 54 may be replaced. This is beneficial since the adaptor 54 may become worn out after a period of time while the tuft assembly 14 may still be useable. The converse may also be true. Alternatively, both the tuft assembly 14 and the adaptor 54 may be replaced at the same time. For example, it may be convenient to provide the tuft assembly 14 and the adaptor 54 as a single unit.

Referring now to FIGS. 5*a* to 5*d*, an alternate embodiment of the tuft assembly 14 and the adaptor 54 is shown, indicated as 14' and 54' respectively. The tuft assembly 14' now comprises an inner recess 86 and a coupling member, which in this embodiment is a groove 88. The diameter of the groove 88 is slightly larger than the diameter of the inner recess 86. Furthermore, the adaptor 54' now comprises a cooperating coupling member, which in this embodiment is a rib 82, a post 83 and a slot 84. The rib 82 and post 83 of the adaptor 54' are dimensioned to movingly engage the groove 88 and the inner recess 86 respectively to ensure that, when the electric toothbrush 10 is active, the adaptor 54' moves relative to the tuft assembly 14' while still urging the tuft assembly 14' to move in a reciprocating fashion around the brush rotation axis 24.

The adaptor 54' and the tuft assembly 14' may now be replaced as one piece (whereas in the previous embodiment one or both of the tuft assembly 14 and the adaptor 54 may be replaced). Alternatively, at least one of the rib 82 and post 83 of the adaptor 54', and the inner recess 86 and the groove 88 may be made of resilient material to allow the adaptor 54' to be attached or detached from the tuft assembly 14' while still allowing the adaptor 54' to be kept in place while the toothbrush 10 is in operation. The adaptor 54' may alternatively have a different outer shape or the slot 84 may not pass throughout the entirety of the adaptor 54'.

In FIGS. 5*a* to 5*d*, there is also a different embodiment of the first and second connection members 56 and 58, now indicated as 90 and 98. The first connection member 90 now has a groove 92, a bore 94 and guide grooves 96. The second connection member 98 now comprises a post 100 and prongs 102 and 104 having ribs 106 and 108 respectively. The first and second connection members 90 and 98 still allow the tuft assembly 14' to be releasably attachable to the support member 20. In particular, the post 100 is dimensioned to be slidably releasably received by the bore 94. In addition, the prongs 102 and 104 are spaced apart from the post 100 so that the ribs 106 and 108 on the prongs 102 and 104 engage the groove 92. The dimensions of the first and second connection members 90 and 98 are also such that these members form a snap-fit connection while still allowing the second connection member 98 to rotate about the first connection member 90. Accordingly, the diameter of the post 100 and the spacing between the ribs 106 and 108 and the groove 92 is sufficient to allow the tuft assembly 14' to reciprocally rotate about the first connection member 90.

Figure 5A:
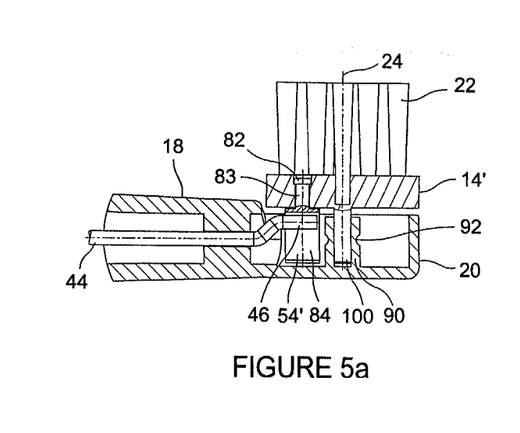
FIG. 5a is a cross-sectional side view of a portion of the electric toothbrush showing another alternate embodiment of the tuft assembly and adaptor.
Figure 5B:
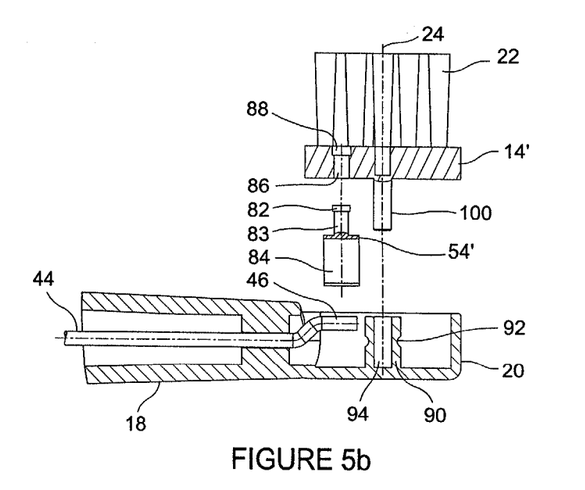
Figure 5C:
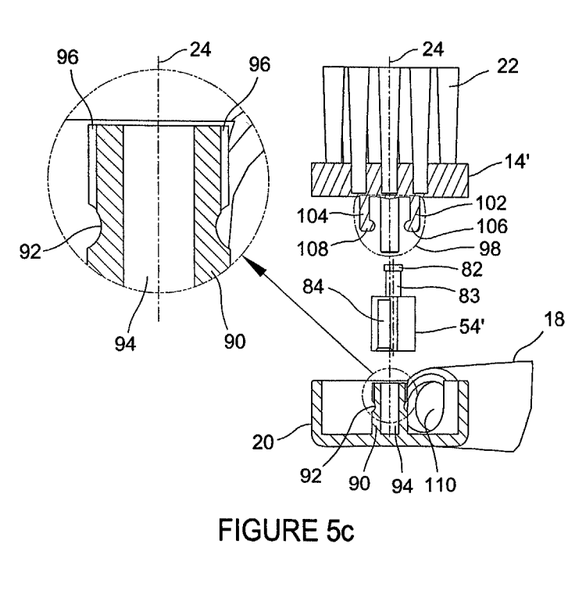
Figure 5D:
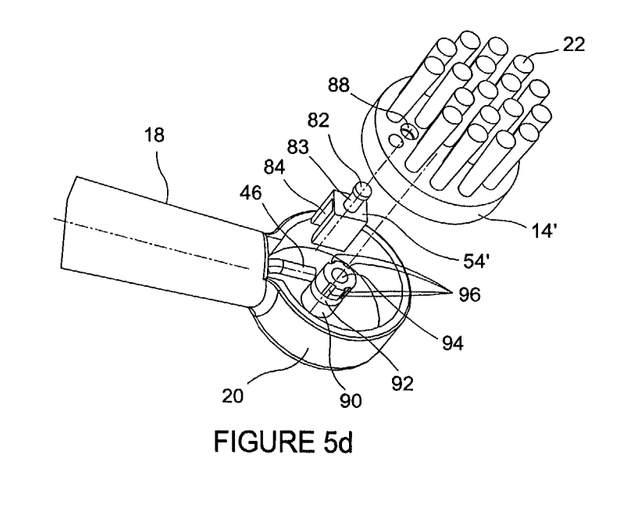
Figure 6A:
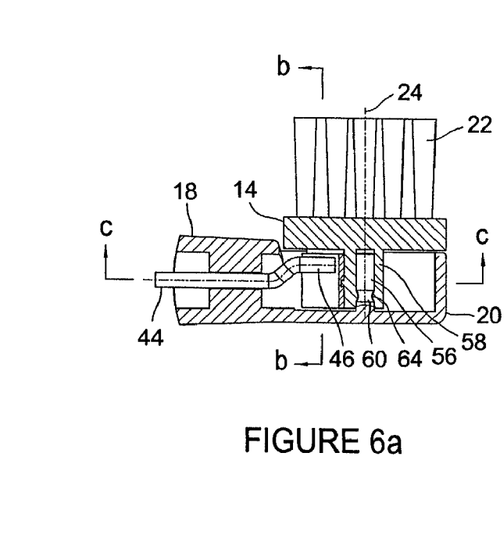
FIG. 6a is a cross-sectional side view of a portion of the electric toothbrush of FIG. 3a with the eccentric end of the transmission at the 12 o'clock position.
Figure 6B:
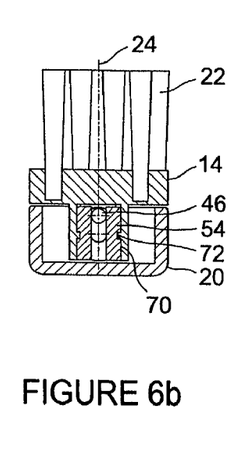
FIG. 6b is a cross-sectional end view of a portion of the electric toothbrush of FIG. 3a with the eccentric end of the transmission at the 12 o'clock position.
Figure 6C:
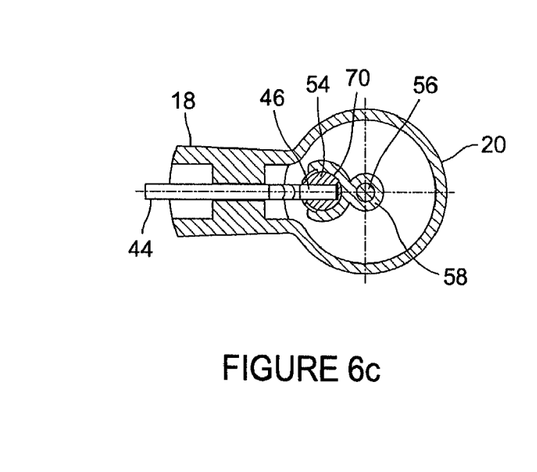
FIG. 6c is a cross-sectional bottom view of a portion of the electric toothbrush of FIG. 3a with the eccentric end of the transmission at the 12 o'clock position.
Figure 6D:
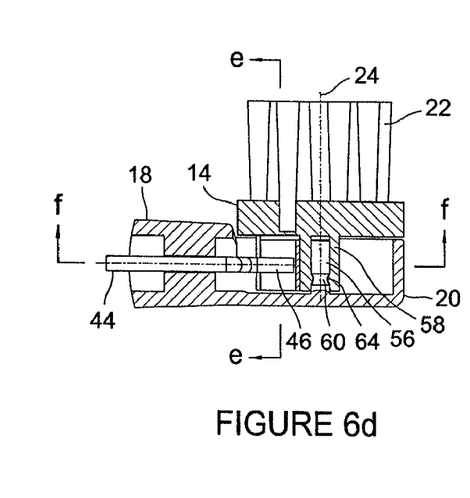
FIG. 6d is a cross-sectional side view of a portion of the electric toothbrush of FIG. 3a with the eccentric end of the transmission at the 3 o'clock position.
Figure 6E:
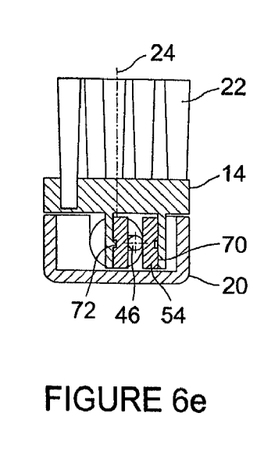
FIG. 6e is a cross-sectional end view of a portion of the electric toothbrush of FIG. 3a with the eccentric end of the transmission at the 3 o'clock position.
Figure 6F:
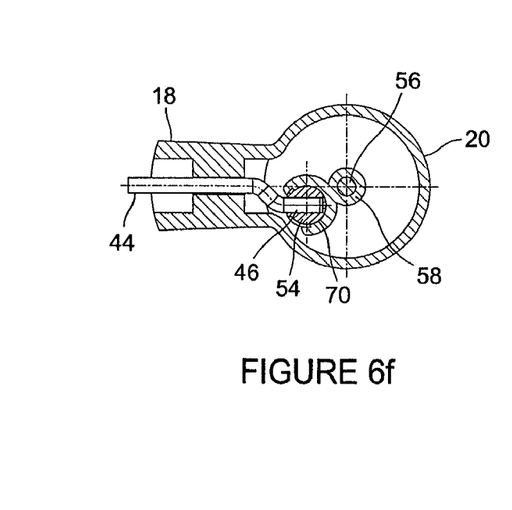
FIG. 6f is a cross-sectional bottom view of a portion of the electric toothbrush of FIG. 3a with the eccentric end of the transmission at the 3 o'clock position.
Figure 6G:
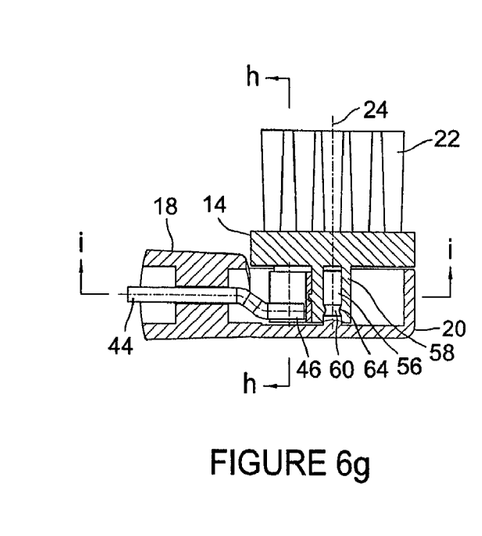
FIG. 6g is a cross-sectional side view of a portion of the electric toothbrush of FIG. 3a with the eccentric end of the transmission at the 6 o'clock position.
Figure 6H:
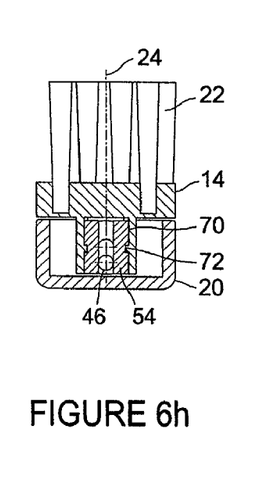
FIG. 6h is a cross-sectional end view of a portion of the electric toothbrush of FIG. 3a with the eccentric end of the transmission at the 6 o'clock position.
Figure 6I:
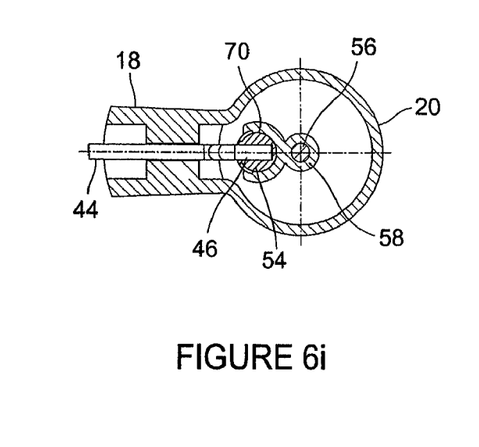
FIG. 6i is a cross-sectional bottom view of a portion of the electric toothbrush of FIG. 3a with the eccentric end of the transmission at the 6 o'clock position.
Figure 6J:
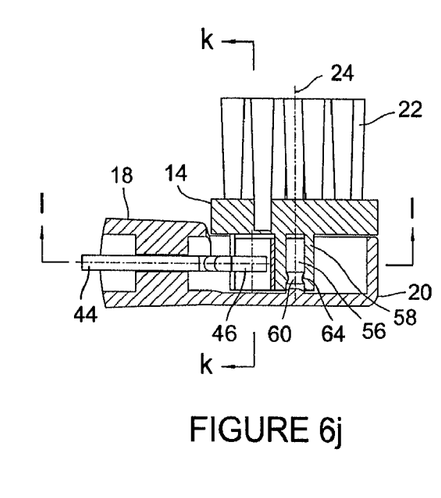
FIG. 6j is a cross-sectional side view of a portion of the electric toothbrush of FIG. 3a with the eccentric end of the transmission at the 9 o'clock position.
Figure 6K:
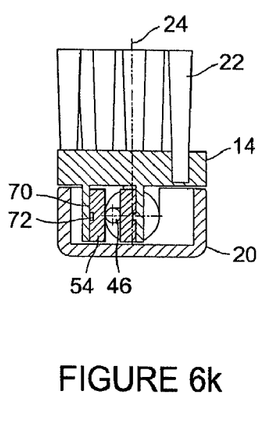
FIG. 6k is a cross-sectional end view of a portion of the electric toothbrush of FIG. 3a with the eccentric end of the transmission at the 9 o'clock position.
Figure 6L:
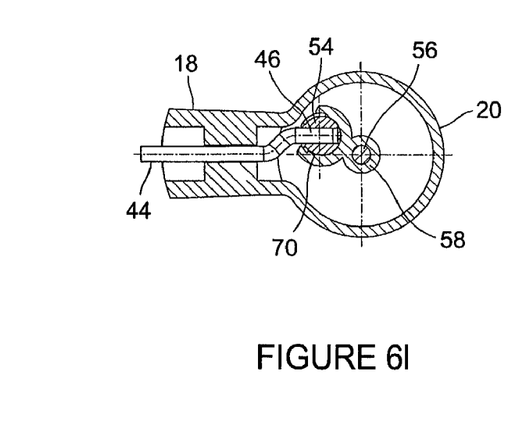
FIG. 6l is a cross-sectional bottom view of a portion of the electric toothbrush of FIG. 3a with the eccentric end of the transmission at the 9 o'clock position.
Figure 7A:
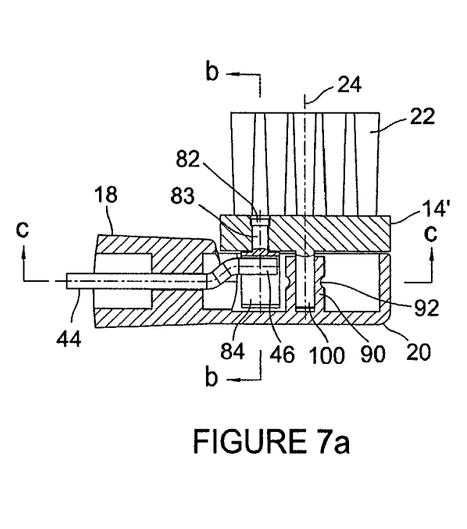
FIG. 7a is a cross-sectional side view of a portion of the electric toothbrush of FIG. 5a with the eccentric end of the transmission at the 12 o'clock position.
Figure 7B:
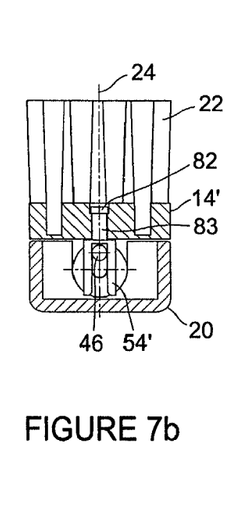
FIG. 7b is a cross-sectional end view of a portion of the electric toothbrush of FIG. 5a with the eccentric end of the transmission at the 12 o'clock position.
Figure 7C:
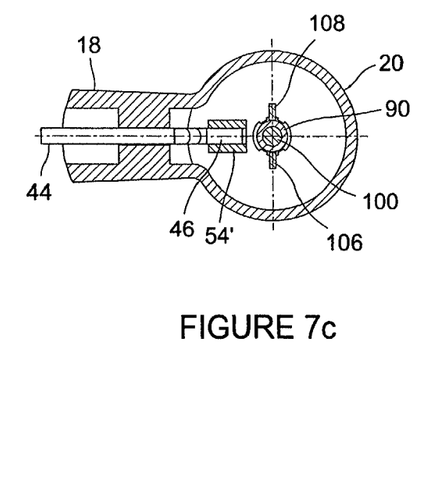
FIG. 7c is a cross-sectional bottom view of a portion of the electric toothbrush of FIG. 5a with the eccentric end of the transmission at the 12 o'clock position.
Figure 7D:
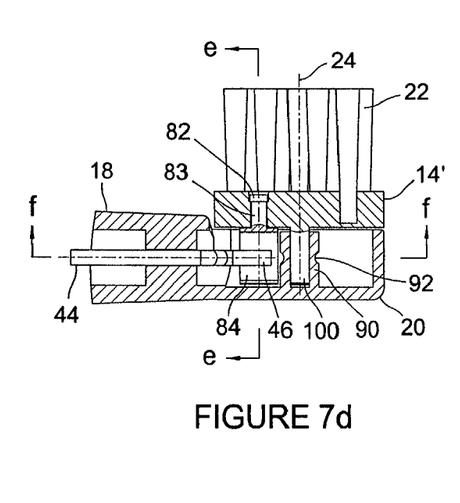
FIG. 7d is a cross-sectional side view of a portion of the electric toothbrush of FIG. 5a with the eccentric end of the transmission at the 3 o'clock position.
Figure 7E:
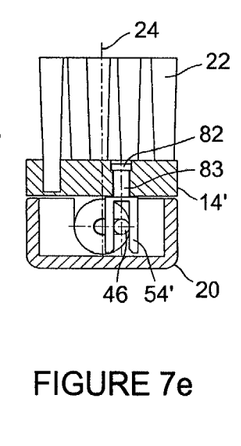
FIG. 7e is a cross-sectional end view of a portion of the electric toothbrush of FIG. 5a with the eccentric end of the transmission at the 3 o'clock position.
Figure 7F:
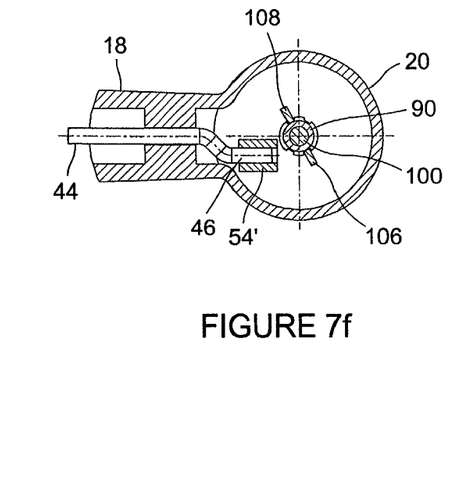
FIG. 7f is a cross-sectional bottom view of a portion of the electric toothbrush of FIG. 5a with the eccentric end of the transmission at the 3 o'clock position.
Figure 7G:
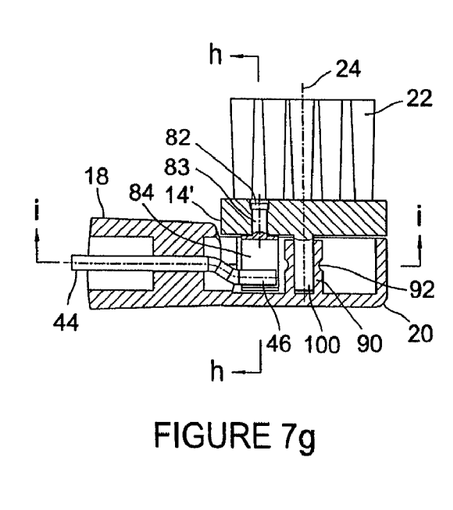
FIG. 7g is a cross-sectional side view of a portion of the electric toothbrush of FIG. 5a with the eccentric end of the transmission at the 6 o'clock position.
Figure 7H:
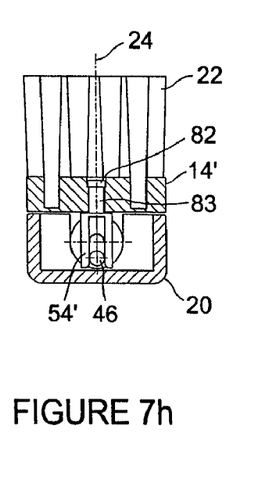
FIG. 7h is a cross-sectional end view of a portion of the electric toothbrush of FIG. 5a with the eccentric end of the transmission at the 6 o'clock position.
Figure 7I:
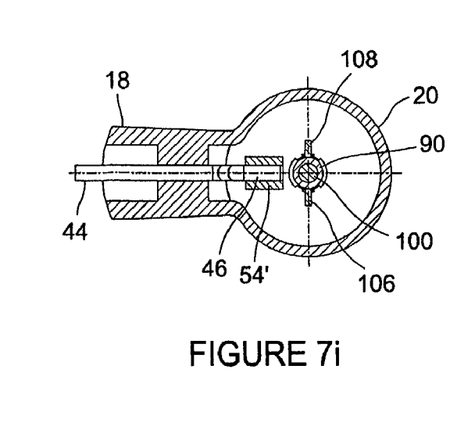
FIG. 7i is a cross-sectional bottom view of a portion of the electric toothbrush of FIG. 5a with the eccentric end of the transmission at the 6 o'clock position.
Figure 7J:
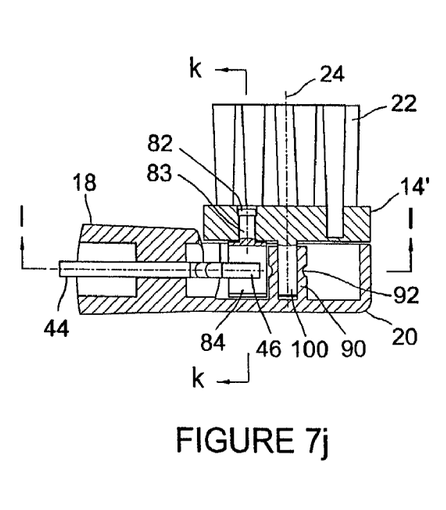
FIG. 7j is a cross-sectional side view of a portion of the electric toothbrush of FIG. 5a with the eccentric end of the transmission at the 9 o'clock position.
Figure 7K:
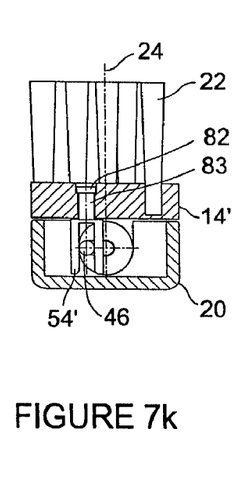
FIG. 7k is a cross-sectional end view of a portion of the electric toothbrush of FIG. 5a with the eccentric end of the transmission at the 9 o'clock position.
Figure 7L:
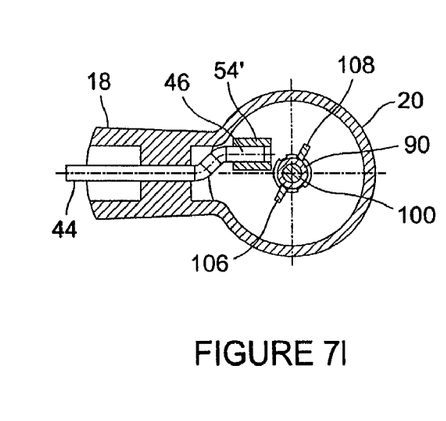
FIG. 7l is a cross-sectional bottom view of a portion of the electric toothbrush of FIG. 5a with the eccentric end of the transmission at the 9 o'clock position.

The guide grooves 96 provide channels through which the ribs 106 and 108 slide when the user of the electric toothbrush 10 is attaching or detaching the tuft assembly 14' and the support member 20. Accordingly, the prongs 102 and 104 must be lined up with the guide grooves 96 when the second connection member 98 is being attached to or detached from the first connection member 90. Also visible from FIG. 5c is an opening 110 through which the eccentric end 46 of the drive shaft 44 protrudes to operatively engage the slot 84 of the adaptor 54'.

In alternative embodiments, the second connection member 98 may only have one prong or more than two prongs. In either case, the number of guide grooves 96 can be adjusted to be twice the number of prongs. Alternatively, there may be a fixed number of guide grooves 96 (such as four guide grooves) so that a variety of tuft assemblies having a different number of prongs may be accommodated. In a further alternative, the first connection member 90 may be located on the tuft assembly 14' and the second connection member 98 may be located on the support member 20.

In use, the drive shaft 44 and the eccentric end 46 provide rotational motion about an axis that is parallel to the motor axis 40. Since the eccentric end 46 is displaced from the motor axis 40, the tip of the eccentric end 46 traces out a circle during one rotation of the drive shaft 44. The radius of this circle is equivalent to the radial displacement of the tip of the eccentric end 46 from the axis of the drive shaft 44. As the tip of the eccentric end 46 traces out this circle in a clockwise fashion, the tip of the eccentric end 46 drives the adaptor 54 (54'), and thus the tuft assembly 14 (14'), in a reciprocating rotating fashion, perpendicular to the slot 66 (84), about the brush rotation axis 24, as will now be described.

Referring now to FIGS. 6a to 6l FIGS. 6a to 6l (which represent the embodiment shown in FIGS. 3a to 3c although the embodiment shown in FIGS. 4a to 4c could also be used) and FIGS. 7a to 7l (which represent the embodiment shown in FIGS. 5a to 5c) show different views of the position of the tuft assembly 14(14') and the adaptor 54 (54') during the operation of the electric toothbrush 10. For orientation purposes, looking along the shaft 18 in a direction away from the tuft assembly 14 (14') (i.e. in the direction shown by any of the arrows b-b, e-e, h-h, and k-k), and considering the start position to be the position of the adaptor 54 (54') when the tip of the eccentric end 46 is at the 12 o'clock position (i.e. FIGS. 6a to 6c and 7a to 7c), as the tip of the eccentric end 46 rotates to the 3 o'clock position, slot 66 (84) in the adaptor 54 (54') travels to the right to its outermost right position (i.e. FIGS. 6d to 6f and 7d to 7f). The tip of the eccentric end 46 then rotates to the 6 o'clock position and the slot 66 (84) in the adaptor 54 (54') travels to the left back to the start position (i.e. FIGS. 6g to 6i and 7g to 7i). As the tip of the eccentric end 46 then rotates to the 9 o'clock position, the slot 66 (84) in the adaptor 54 (54') travels to the left to its outermost left position (i.e. FIGS. 6j to 6l and 7j to 7l ) and as the tip of the eccentric end 46 then rotates to the 12 o'clock position, the slot 66 (84) in the adaptor 54 (54') travels to the right back to the starting position (i.e. FIGS. 6a to 6c and 7a to 7c). Thus during one rotation of the drive shaft 44, the tuft assembly 14 (14') performs one cycle of forward and backward cleaning action. Alternatively, the eccentric end 46 may trace out this circle in a counterclockwise fashion.

FIGS. 6c, 6f, 6i, 6l and FIGS. 7c, 7f, 7i and 7l show that the eccentric end 46 remains fully engaged in (i.e. in full alignment with) the adaptor 54 (54') since the adaptor 54 (54') is able to pivot relative to the tuft assembly 14 (14'). Furthermore, if the transmission 42 were to drive the adaptor 54 (54') in a reciprocating rotational fashion, then the adaptor 54 (54') would simply transfer this reciprocating rotational motion to the tuft assembly 14 (14'). Accordingly, due to the physical arrangement between the adaptor 54 (54') and the tuft assembly 14 (14'), the adaptor 54 (54') can accommodate both a continuously rotating and a reciprocally rotating transmission (i.e. the transmission 42 may provide rotational motion that is continuous or reciprocating).

Figure 8A:
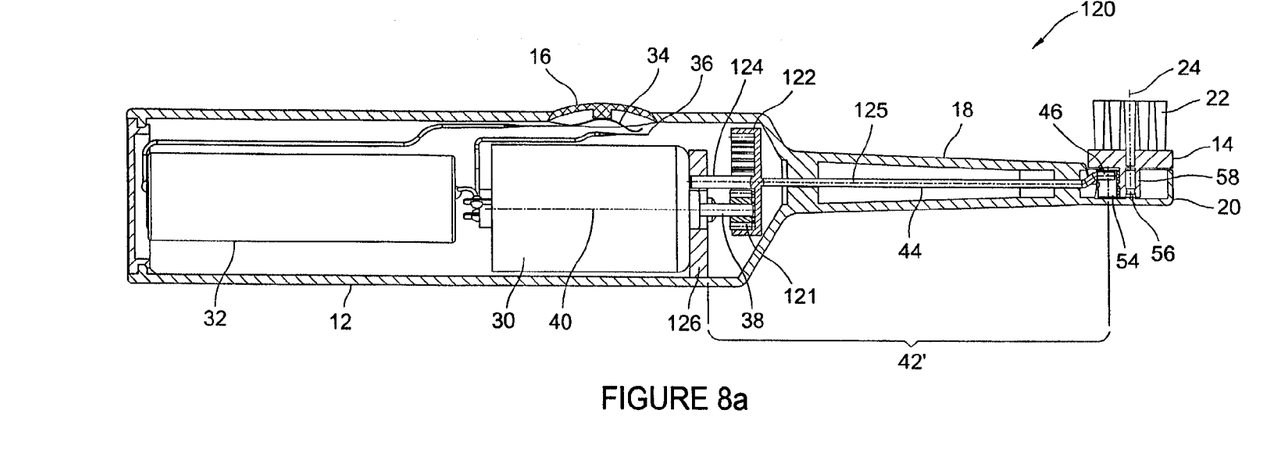
FIG. 8a is a cross-sectional side view of an alternate embodiment of the electric toothbrush having an alternate transmission.
Figure 8B:
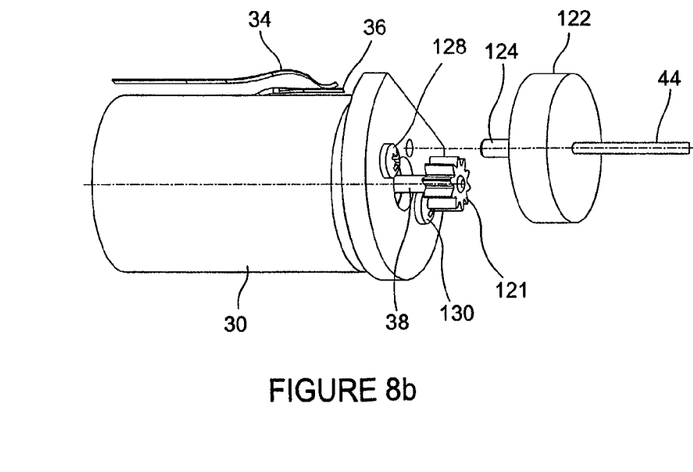
Figure 8C:
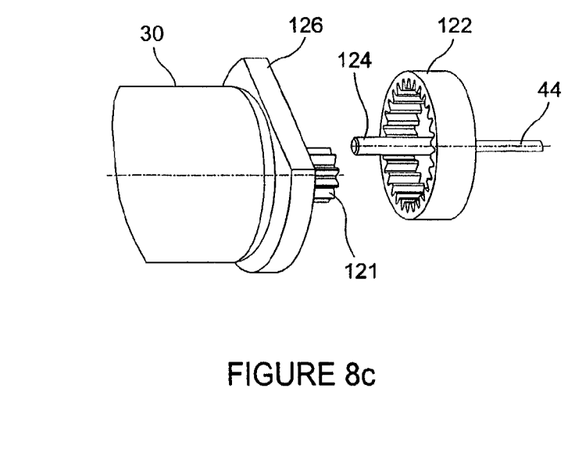

Referring now to FIGS. 8a to 8c, shown therein is an alternative embodiment of an electric toothbrush 120 having an alternate transmission 42'. The rest of the components of the electric toothbrush 120 are similar to those of the electric toothbrush 10 and will not be described. The transmission 42' comprises a speed transformer to modify the rotational speed of the tuft assembly 14 with respect to the rotational speed of the output shaft 38. The transmission 42' comprises the drive shaft 44 having the eccentric end 46, the speed transformer comprising pinion gear 121, inner gear 122, and shaft 124. The pinion gear 121 is mounted on the output shaft 38 of the electric motor 30 such that the drive rotation axis 125 is offset from the motor axis 40. The inner gear 122 is mounted on the shaft 124 which is rotatably mounted on plate 126. The plate 126 is secured to the electric motor 30 via fastening means 128 and 130 which may be screws or the like. The pinion gear 121 meshes with the inner gear 122 to cause the inner gear 122 to rotate when the output shaft 38 rotates. The inner gear 122 has a face from which the drive shaft 44 extends to receive the rotational motion of the inner gear 122 and transfer the rotational motion to the tuft assembly 14. The relative radii of the pinion gear 121 and the inner gear 122 may be selected to achieve a desired rotational speed for the tuft assembly 14 based on the rotational speed of the output shaft 38 as is well known to those skilled in the art. Either of the embodiments of the tuft assembly 14, 14', the adaptor 54, 54', and the first and second connection members 56, 90 and 58, 98 may be used with the transmission 42' (although the tuft assembly 14, the adaptor 54 and the first and second connection members 56 and 58 from FIGS. 3a to 3c are shown in FIG. 8a).

Figure 9A:
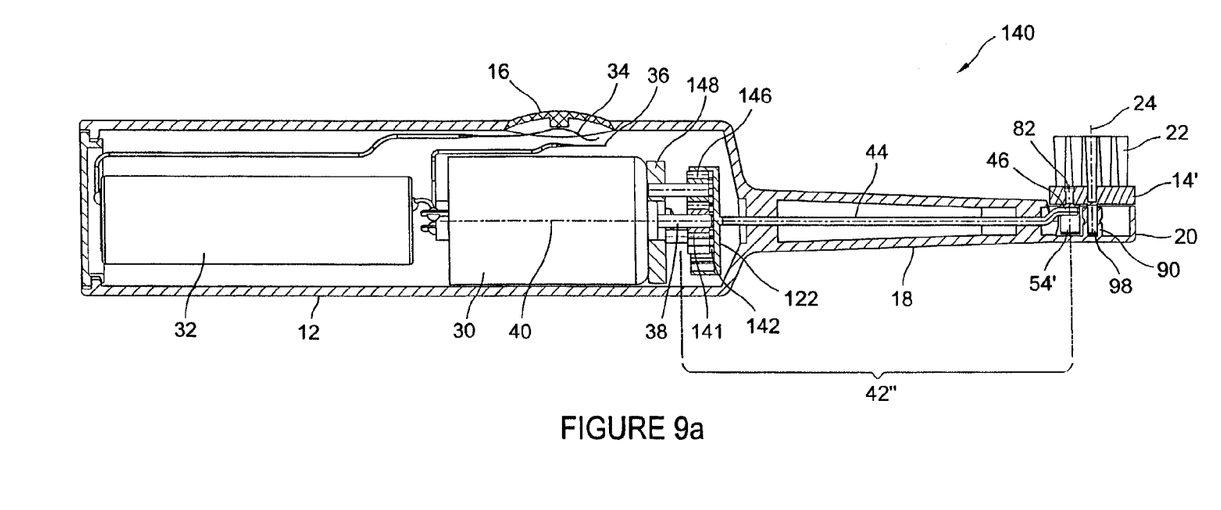
FIG. 9a is a cross-sectional side view of an alternate embodiment of the electric toothbrush having another alternate transmission.
Figure 9B:
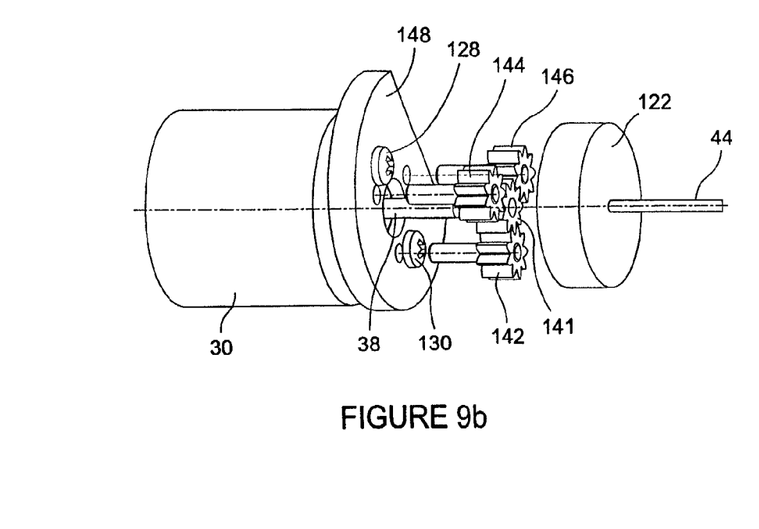
Figure 9C:
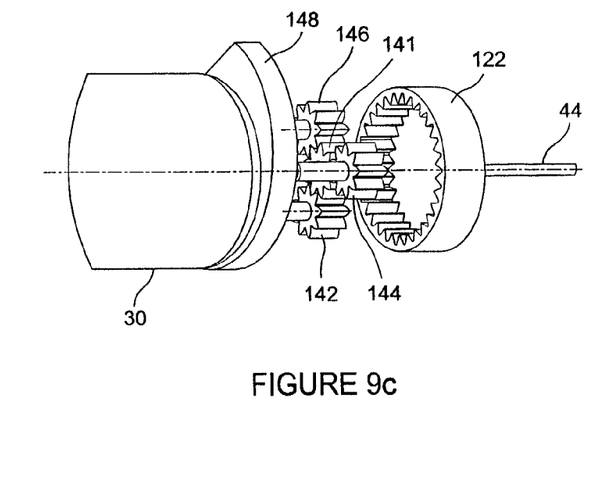

Referring now to FIGS. 9a to 9c, shown therein is an alternative embodiment of an electric toothbrush 140 having an alternate transmission 42". The rest of the components of the electric toothbrush 140 are similar to those of the electric toothbrush 10 and will not be described. The transmission 42" comprises an alternative speed transformer to modify the rotational speed of the tuft assembly 14' with respect to the rotational speed of the output shaft 38. The transmission 42" comprises the drive shaft 44 having the eccentric end 46 and the speed transformer comprising central gear 141, satellite gears 142, 144 and 146 and inner gear 122 The central gear 141 is mounted on the output shaft 38 of the electric motor 30. The satellite gears 142, 144 and 148 are mounted on shafts that are uniformly distributed about the central gear 141. These shafts are rotatably mounted on plate 148. The inner gear 122 is mounted so that each one of the satellite gears 142, 144 and 146 meshes with the inner gear 122 to cause the inner gear 122 to rotate when the output shaft 38 rotates. The inner gear 122 has a face from which the drive shaft 44 extends to receive the rotational motion of the inner gear 122 and transfer the rotational motion to the tuft assembly 14'. The relative radii of the central gear 141, the satellite gears 142, 144 and 146, and the inner gear 122 may be selected to achieve a desired rotational speed for the tuft assembly 14' based on the rotational speed of the output shaft 38 as is well known to those skilled in the art. Either of the embodiments of the tuft assembly 14, 14', the adaptor 64, 54', and the first and second connection members 56, 90 and 58, 98 may be used with the transmission 42" (although the tuft assembly 14'. the adaptor 54' and the first and second connection members 90 and 98 from FIGS. 5*a* to 5*d* are shown in FIG. 9*a*).

It should be understood that various modifications can be made to the preferred embodiments described and illustrated herein, without departing from the present invention, the scope of which is defined in the appended claims.

The invention claimed is:

1. An electric toothbrush, comprising:
   a) a main body;
   b) a tuft assembly connected to the main body;
   c) an electric motor mounted in the main body;
   d) a transmission having a first end and an eccentric end, the first end being operatively connected to the electric motor, the transmission being adapted to rotate; and
   e) an adaptor rotatably coupled to the tuft assembly about a pivot axis, the adaptor having a slot with two planar parallel sidewalls dimensioned to slidably receive the eccentric end of the transmission so that the eccentric end is in alignment with the slot while the transmission is rotating, the pivot axis of the adaptor extending through the slot so that as the transmission rotates the adaptor imparts oscillatory rotational movement to the tuft assembly.

2. The electric toothbrush of claim 1, wherein the tuft assembly further comprises an inner recess, and the adaptor is dimensioned to be releasably received in the inner recess.

3. The electric toothbrush of claim 2, wherein the adaptor further comprises a first coupling member positioned on the outer surface of the adaptor, the tuft assembly further comprises a second coupling member positioned on the inner recess, and the first and second coupling members are dimensioned to permit the inner recess of the tuft assembly to releasably receive the adaptor.

4. The electric toothbrush of claim 3, wherein one of the coupling members is at least one groove and the other of the coupling members is at least one rib.

5. The electric toothbrush of claim 2, wherein the inner recess is eccentrically positioned in relation to a pivot axis of the tuft assembly.

6. The electric toothbrush of claim 5, wherein the adaptor further comprises a first coupling member positioned on the outer surface of the adaptor, the tuft assembly further comprises a second coupling member positioned on the inner recess, and the first and second coupling members are dimensioned to permit the inner recess of the tuft assembly to releasably receive the adaptor.

7. The electric toothbrush of claim 6, wherein one of the coupling members is at least one groove and the other of the coupling members is at least one rib.

8. The electric toothbrush of claim 1, further comprising a support member connected to the main body, the support member having a first connection member, the tuft assembly having a second connection member, and one of the connection members having an elongate body with a groove on the outer surface thereof and the other of said connection members has at least one protrusion adapted to releasably engage the groove.

9. The electric toothbrush of claim 8, wherein the at least one protrusion Comprises a cylindrical body having an inner channel with a rib on an inner surface thereof, the inner channel and the rib dimensioned to releasably engage said elongate body and allow for rotational movement of the tuft assembly.

10. The electric toothbrush of claim 8, wherein the elongate body has a bore, and the at least one protrusion comprises a post and at least one prong having one rib, the post dimensioned to slidably engage the bore and the at least one prong being spaced apart from the post to releasaby engage the groove on the outer surface of the elongate body and allow for rotational movement of said tuft assembly.

11. The electric toothbrush of claim 1, wherein the pivot axis of the adaptor is positioned at a right angle to the eccentric end of the transmission.

* * * * *